US012590047B2

(12) United States Patent
Nozaki et al.

(10) Patent No.: US 12,590,047 B2
(45) Date of Patent: Mar. 31, 2026

(54) METHOD FOR PRODUCING FLUORINE-CONTAINING OLEFIN

(71) Applicants: THE UNIVERSITY OF TOKYO, Tokyo (JP); AGC INC., Tokyo (JP)

(72) Inventors: Kyoko Nozaki, Bunkyo-ku (JP); Midori Akiyama, Bunkyo-ku (JP); Kenta Mori, Bunkyo-ku (JP); Takashi Okazoe, Chiyoda-ku (JP); Yuichiro Ishibashi, Chiyoda-ku (JP); Ko Inada, Chiyoda-ku (JP)

(73) Assignees: THE UNIVERSITY OF TOKYO, Tokyo (JP); AGC INC., Tokyo (JP)

( * ) Notice: Subject to any disclaimer, the term of this patent is extended or adjusted under 35 U.S.C. 154(b) by 824 days.

(21) Appl. No.: 17/891,336

(22) Filed: Aug. 19, 2022

(65) Prior Publication Data

US 2023/0016405 A1 Jan. 19, 2023

Related U.S. Application Data

(63) Continuation of application No. PCT/JP2021/005343, filed on Feb. 12, 2021.

(30) Foreign Application Priority Data

Mar. 2, 2020 (JP) ................................ 2020-034736
Aug. 4, 2020 (JP) ................................ 2020-132483

(51) Int. Cl.

| | |
|---|---|
| ***C07C 41/22*** | (2006.01) |
| ***B01J 31/22*** | (2006.01) |
| ***C07C 17/263*** | (2006.01) |
| ***C07C 319/20*** | (2006.01) |
| ***C07D 209/86*** | (2006.01) |

(52) U.S. Cl.

CPC ........... *C07C 41/22* (2013.01); *B01J 31/2217* (2013.01); *B01J 31/2278* (2013.01); *C07C 17/2637* (2013.01); *C07C 319/20* (2013.01); *C07D 209/86* (2013.01); *B01J 2231/4288* (2013.01); *B01J 2531/821* (2013.01)

(58) Field of Classification Search

CPC .............................. C07C 41/22; C07D 209/86

See application file for complete search history.

(56) References Cited

U.S. PATENT DOCUMENTS

2005/0014916 A1 1/2005 Sakamoto et al.
2016/0176791 A1 6/2016 Takahira
2017/0101360 A1 4/2017 Takahira
2018/0086684 A1 3/2018 Takahira

FOREIGN PATENT DOCUMENTS

JP 2003-089689 A 3/2003
JP 2003-096167 A 4/2003
WO WO 2015/033927 A1 3/2015

OTHER PUBLICATIONS

International Search Report issued Mar. 30, 2021 in PCT/JP2021/005343 filed on Feb. 12, 2021, 3 pages.

Buchmeiser et al., "Pseudo-Halide and Nitrate Derivatives of Grubbs and Grubbs-Hoveyda Initiators: Some Structural Features Related to the Alternating Ring-Opening Metathesis Copolymerization of Norborn-2-ene with Cyclic Olefins", Macromolecules, vol. 44, 2011, pp. 4098-4106.

Yusuke Takahira et al.: "Ruthenium-Catalyzed Olefin Cross-Metathesis with Tetrafluoroethylene and Analogous Fluoroolefins", Journal of the American Chemical Society, vol. 137, No. 22, Jun. 10, 2015 (Jun. 10, 2015), pp. 7031-7034.

*Primary Examiner* — Shawquia Jackson

(74) *Attorney, Agent, or Firm* — Oblon, McClelland, Maier & Neustadt, L.L.P.

(57) ABSTRACT

A production method of producing a fluorine-containing olefin by allowing a first olefin represented by the following Formula (1) and a second olefin to react with each other in the presence of a ruthenium compound represented by the following Formula (X) is provided.

(X)

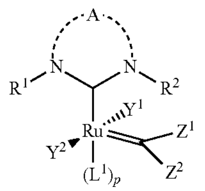

(1)

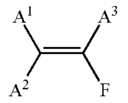

15 Claims, No Drawings

METHOD FOR PRODUCING FLUORINE-CONTAINING OLEFIN

CROSS-REFERENCE TO RELATED APPLICATION

This application is a Continuation of International Application No. PCT/JP2021/005343, filed Feb. 12, 2021, which claims priority to Japanese Patent Application No. 2020-034736 filed Mar. 2, 2020 and Japanese Patent Application No. 2020-132483 filed Aug. 4, 2020. Each of the above applications is hereby expressly incorporated by reference, in its entirety, into the present application.

TECHNICAL FIELD

The present disclosure relates to a method of producing a fluorine-containing olefin.

BACKGROUND ART

Compounds in which some or all of hydrogen atoms in an olefin are substituted with fluorine atoms, that is, fluorine-containing olefins are known as compounds useful in industry.

For example, International Publication No. WO 2015/033927 describes, as a method of producing a fluorine-containing olefin, a production method by a metathesis reaction between an olefin having at least two fluorine atoms and another olefin in the presence of a ruthenium compound.

SUMMARY OF THE INVENTION

Technical Problem

In International Publication No. WO 2015/033927, a ruthenium compound including a 5-membered N-heterocyclic carbene ligand is used as a catalyst, and the metathesis reaction is confirmed to proceed. However, improvement in yield has been demanded.

The present disclosure was made under such circumstances, and a problem to be solved by one embodiment of the present invention is to provide a method of producing a fluorine-containing olefin, by which a fluorine-containing olefin can be obtained at a high yield.

Specific means for solving the problem includes the following aspects.

<1> A production method of producing a fluorine-containing olefin by allowing a first olefin represented by the following Formula (1) and a second olefin different from the first olefin to react with each other in the presence of a ruthenium compound represented by the following Formula (X):

(X)

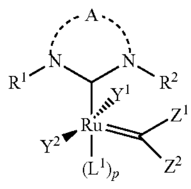

wherein in Formula (X),

A represents an atom group necessary for forming a 6- or 7-membered nitrogen-containing heterocyclic ring including two nitrogen atoms, an aromatic or aliphatic ring may be condensed to the nitrogen-containing heterocyclic ring, and A and the aromatic or aliphatic ring condensed to the nitrogen-containing heterocyclic ring may include a substituent, each of $R^1$ and $R^2$ independently represents an alkyl group, an aryl group, or an aralkyl group, each of $Y^1$ and $Y^2$ independently represents an anionic ligand, $L^1$ represents a neutral electron-donating ligand, p represents 0 or 1, each of $Z^1$ and $Z^2$ independently represents a hydrogen atom, a halogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, $Z^1$ and $Z^2$ may be bonded to each other to form a ring, and either or both of $Z^1$ and $Z^2$, and $L^1$ may be chemically bonded to each other, and (1)

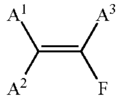

in Formula (1), each of $A^1$, $A^2$, and $A^3$ independently represents a hydrogen atom, a fluorine atom, a chlorine atom, or a fluorine-containing alkyl group having a carbon number of from 1 to 10.

<2> The production method according to <1>, wherein the second olefin is represented by the following Formula (2):

(2)

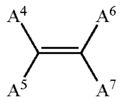

wherein in Formula (2), at least one of $A^4$ to $A^7$ represents a functional group AA including an oxygen atom, a nitrogen atom, a sulfur atom, or a phosphorus atom at a linkage position to vinyl carbon, each of $A^4$ to $A^7$, other than the functional group AA, independently represents a hydrogen atom, a halogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, and $A^4$ and $A^5$, $A^4$ and $A^6$, $A^5$ and $A^7$, or $A^6$ and $A^7$ may be bonded to each other to form a ring, and in a case in which one of $A^4$ or $A^5$ is a halogen atom, another one of $A^4$ or $A^5$ represents a hydrogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, and in a case in which one of $A^6$ or $A^7$ is a halogen atom, another one of $A^6$ or $A^7$ represents a hydrogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom.

<3> The production method according to <2>, wherein in Formula (2), the functional group AA is an alkoxy group having a carbon number of from 1 to 20 or an aryloxy group having a carbon number of from 6 to 20.

<4> The production method according to any one of <1> to <3>, wherein in Formula (1), at least two of $A^1$, $A^2$, or $A^3$ are fluorine atoms.

<5> The production method according to any one of <1> to <4>, wherein the second olefin is a monosubstituted olefin or a 1,2-disubstituted olefin.

<6> The production method according to any one of <1> to <5>, wherein an amount of the ruthenium compound used is from 0.001% by mol to 1.0% by mol with respect to a substance amount of the second olefin.

<7> The production method according to any one of <1> to <6>, wherein, in Formula (X), each of $R^1$ and $R^2$ is independently a 2,4,6-trimethylphenyl group, a 2,6-diisopropylphenyl group, an o-tolyl group, a 3,5-di-tert-butylphenyl group, a 2,6-dimethyl-4-methoxyphenyl group, or a 2,6-difluorophenyl group.

Advantageous Effects of the Invention

According to the present disclosure, a method of producing a fluorine-containing olefin, by which a fluorine-containing olefin can be obtained at a high yield, is provided.

DESCRIPTION OF EMBODIMENTS

A method of producing a fluorine-containing olefin of the present disclosure is described in detail below.

In the present specification, a numerical range expressed by "x to y" means a range including the values of x and y as the minimum and maximum values, respectively.

In a numerical range expressed in a stepwise manner in the present specification, the upper or lower limit value expressed in a certain numerical range may be replaced by the upper or lower limit value in another numerical range expressed in a stepwise manner. In a numerical range expressed in the present specification, the upper or lower limit value expressed in a certain numerical range may be replaced by values described in Examples.

In the present specification, in a case in which plural kinds of substances corresponding to each component exist in the composition, the amount of each component in the composition means, unless otherwise specified, the total amount of the plural kinds of substances existing in the composition.

In the present specification, a combination of two or more preferred aspects is a more preferred aspect.

The term "step" herein encompasses not only an independent step but also a step of which the desired object is achieved even in a case in which the step is incapable of being definitely distinguished from another step.

[Method of Producing Fluorine-Containing Olefin]

The method of producing a fluorine-containing olefin of the present disclosure is a production method of producing a fluorine-containing olefin by allowing a first olefin represented by the following Formula (1) and a second olefin different from the first olefin to react with each other in the presence of a ruthenium compound represented by the following Formula (X).

(X)

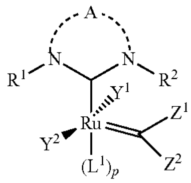

In Formula (X), A represents an atom group necessary for forming a 6- or 7-membered nitrogen-containing heterocyclic ring including two nitrogen atoms. An aromatic or aliphatic ring may be condensed to the nitrogen-containing heterocyclic ring. A and the aromatic or aliphatic ring condensed to the nitrogen-containing heterocyclic ring may include a substituent.

Each of $R^1$ and $R^2$ independently represents an alkyl group, an aryl group, or an aralkyl group.

Each of $Y^1$ and $Y^2$ independently represents an anionic ligand.

$L^1$ represents a neutral electron-donating ligand.

In Formula (X), p represents 0 or 1.

Each of $Z^1$ and $Z^2$ independently represents a hydrogen atom, a halogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, and $Z^1$ and $Z^2$ may be bonded to each other to form a ring. Either or both of $Z^1$ and $Z^2$, and $L^1$ may be chemically bonded to each other.

(1)

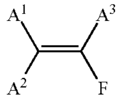

In Formula (1), each of $A^1$, $A^2$, and $A^3$ independently represents a hydrogen atom, a fluorine atom, a chlorine atom, or a fluorine-containing alkyl group having a carbon number of from 1 to 10.

It was found that in the method of producing a fluorine-containing olefin of the present disclosure, use of the ruthenium compound represented by Formula (X) as a catalyst allows a metathesis reaction between the first olefin represented by Formula (1) and the second olefin to proceed, whereby a yield is significantly improved in comparison with yields in conventional methods. The reason of the improvement in yield is unclear, and is considered to be that the nitrogen-containing heterocyclic ring bonded to ruthenium in Formula (X) is the 6- or 7-membered ring. Specifically, it is considered that an electron density on the ruthenium atom is increased to achieve an electronic state optimal for the metathesis reaction of the fluorine-containing olefin because a complex including a 6- or 7-membered ring N-heterocyclic carbene ligand has a higher electron-donating ability than a complex including a 5-membered N-heterocyclic carbene ligand.

Each raw material used in the method of producing a fluorine-containing olefin of the present disclosure is described below.

Ruthenium Compound Represented by Formula (X)

The ruthenium compound used in the method of producing a fluorine-containing olefin of the present disclosure is represented by the following Formula (X). In the method of producing a fluorine-containing olefin of the present disclosure, the ruthenium compound represented by Formula (X) functions as a catalyst.

(X)

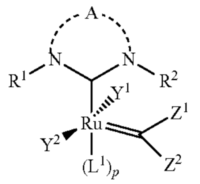

[A]

In Formula (X), A represents an atom group necessary for forming a 6- or 7-membered nitrogen-containing heterocyclic ring including two nitrogen atoms. A preferably includes a combination of atoms selected from the group consisting of a carbon atom, a nitrogen atom, and an oxygen atom, and is more preferably composed of only carbon atoms. In other words, A preferably represents a carbon atom group necessary for forming the 6- or 7-membered nitrogen-containing heterocyclic ring including two nitrogen atoms.

In a case in which the 6- or 7-membered nitrogen-containing heterocyclic ring is composed of two nitrogen atoms and a carbon atom group, the carbon atom group may be saturated or unsaturated, and is preferably saturated. Carbon atoms included in the carbon atom group may be carbonyl carbon. A is preferably an alkylene group, and more preferably a trimethylene group or a tetramethylene group.

A may include a substituent. Examples of the substituent include an alkyl group, an alkenyl group, an alkynyl group, an aryl group, an aralkyl group, a heterocyclic group, a halogen atom, an alkoxy group, an aryloxy group, an amino group, a nitrile group, a nitro group, a sulfo group, a carboxy group, and a hydroxy group. These substituents may further include the substituents described above.

The alkyl group may be cyclic or a chain. The chain alkyl group may be a straight-chain alkyl group or a branched-chain alkyl group. The carbon number of the alkyl group is preferably from 1 to 20, more preferably from 1 to 12, and still more preferably from 1 to 8. Examples of the alkyl group include methyl group, ethyl group, n-propyl group, isopropyl group, n-butyl group, tert-butyl group, cyclopropyl group, cyclohexyl group, and 2-ethylhexyl group. Examples of the alkyl group including a substituent include 2-hydroxyethyl group, 2-carboxyethyl group, 2-methoxyethyl group, and 2-diethylaminoethyl group.

The alkenyl group may be cyclic or a chain. The chain alkenyl group may be a straight-chain alkenyl group or a branched-chain alkenyl group. The carbon number of the alkenyl group is preferably from 2 to 20, more preferably from 2 to 12, and still more preferably from 2 to 8. Examples of the alkenyl group include vinyl group, allyl group, 1-propenyl group, 2-butenyl group, 2-pentenyl group, and 2-hexenyl group.

The alkynyl group may be cyclic or a chain. The chain alkynyl group may be a straight-chain alkynyl group or a branched-chain alkynyl group. The carbon number of the alkynyl group is preferably from 2 to 20, more preferably from 2 to 12, and still more preferably from 2 to 8. Examples of the alkynyl group include ethynyl group and 2-propynyl group.

Examples of the aryl group include phenyl group and naphthyl group. Examples of the aryl group including a substituent include 2,4,6-trimethylphenyl group, 2,6-diisopropylphenyl group, o-tolyl group, 3,5-di-tert-butylphenyl group, 2,6-dimethyl-4-methoxyphenyl group, and 2,6-difluorophenyl group.

The alkyl moiety of the aralkyl group is similar to the alkyl group. The aryl moiety of the aralkyl group is similar to the aryl group. Examples of the aralkyl group include benzyl group and phenethyl group.

The heterocycle of the heterocyclic group is preferably a 5-membered ring or a 6-membered ring. The heterocycle may be a monocycle or a condensed ring. Examples of the heterocycle include a pyridine ring, a piperidine ring, a furan ring, a furfuran ring, a thiophene ring, a pyrrole ring, a quinoline ring, a morpholine ring, an indole ring, an imidazole ring, a pyrazole ring, a carbazole ring, a phenothiazine ring, a phenoxazine ring, an indoline ring, a thiazole ring, a pyrazine ring, a thiadiazine ring, a benzoquinoline ring, and a thiadiazole ring.

Examples of the halogen atom include a fluorine atom, a chlorine atom, a bromine atom, and an iodine atom.

The alkyl moiety of the alkoxy group is similar to the alkyl group. Examples of the alkoxy group include methoxy group, propyloxy group, pentyloxy group, and cyclohexyl oxy group.

The aryl moiety of the aryloxy group is similar to the aryl group. Examples of the aryloxy group include phenoxy group and naphthyloxy group.

An aromatic ring or an aliphatic ring may be condensed to the nitrogen-containing heterocyclic ring, and the aromatic ring or the aliphatic ring that is condensed to the nitrogen-containing heterocyclic ring may include a substituent. Examples of the substituent included in the aromatic ring or the aliphatic ring include substituents similar to the substituent included in A as described above.

Examples of the aromatic ring that may be condensed to the nitrogen-containing heterocyclic ring include a benzene ring and a naphthalene ring. Examples of the aliphatic ring that may be condensed to the nitrogen-containing heterocyclic ring include a cyclopentane ring and a cyclohexane ring.

[$R^1$ and $R^2$]

In Formula (X), each of $R^1$ and $R^2$ independently represents an alkyl group, an aryl group, or an aralkyl group. Each of the alkyl group, the aryl group, and the aralkyl group may include a substituent. Examples of the substituent include substituents similar to the substituent included in A as described above.

The alkyl group may be cyclic or a chain. The chain alkyl group may be a straight-chain alkyl group or a branched-chain alkyl group. The carbon number of the alkyl group is preferably from 1 to 20, more preferably from 1 to 12, and still more preferably from 1 to 8. Examples of the alkyl group include methyl group, ethyl group, n-propyl group, isopropyl group, n-butyl group, tert-butyl group, cyclopropyl group, cyclohexyl group, and 2-ethylhexyl group. Examples of the alkyl group including a substituent include 2-hydroxyethyl group, 2-carboxyethyl group, 2-methoxyethyl group, and 2-diethylaminoethyl group.

Examples of the aryl group include phenyl group and naphthyl group. Examples of the aryl group including a substituent include 2,4,6-trimethylphenyl group, 2,6-diisopropylphenyl group, o-tolyl group, 3,5-di-tert-butylphenyl group, 2,6-dimethyl-4-methoxyphenyl group, and 2,6-difluorophenyl group.

The alkyl moiety of the aralkyl group is similar to the alkyl group. The aryl moiety of the aralkyl group is similar to the aryl group. Examples of the aralkyl group include benzyl group and phenethyl group.

From the viewpoint of improving catalytic activity, $R^1$ and $R^2$ are preferably three-dimensionally bulky groups, more preferably branched-chain alkyl groups, cyclic alkyl groups, aryl groups, or aralkyl groups, still more preferably cyclic alkyl groups, awl groups, or aralkyl groups, and particularly preferably aryl groups.

Specifically, the branched-chain alkyl group is preferably tert-butyl group. The cyclic alkyl group is preferably a cycloalkyl group. The aryl group is preferably 2,4,6-trimethylphenyl group, 2,6-diisopropylphenyl group, o-tolyl group, 3,5-di-tert-butylphenyl group, 2,6-dimethyl-4-methoxyphenyl group, or 2,6-difluorophenyl group. The aralkyl group is preferably benzyl group.

[$Y^1$ and $Y^2$]

In Formula (X), each of $Y^1$ and $Y^2$ independently represents an anionic ligand. The anionic ligand is a ligand having a negative charge in the case of being separated from a ruthenium atom. Examples of $Y^1$ and $Y^2$ include a halogen atom. Especially, $Y^1$ and $Y^2$ are more preferably chlorine atoms.

[$L^1$]

In Formula (X), $L^1$ represents a neutral electron-donating ligand. The electron-donating ligand is a ligand having the effect of increasing the electron density of a ruthenium atom.

Examples of the electron-donating ligand include a nitrogen-based ligand, a phosphorus-based ligand, and an oxygen-based ligand.

Examples of the nitrogen-based ligand include a bipyridine-based ligand, a biquinoline-based ligand, a phenanthroline-based ligand, a pyridine-based ligand, a quinoline-based ligand, a benzoquinoline-based ligand, an acridine-based ligand, a tertiary aliphatic amine-based ligand, and a tertiary aromatic amine-based ligand. Examples of the phosphorus-based ligand include a phosphine-based ligand. Examples of the oxygen-based ligand include an ether-based ligand.

[p]

In Formula (X), p represents 0 or 1. In other words, $L^1$ is optionally present.

[$Z^1$ and $Z^2$]

In Formula (X), each of $Z^1$ and $Z^2$ independently represents a hydrogen atom, a halogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, and $Z^1$ and $Z^2$ may be bonded to each other to form a ring. Either or both of $Z^1$ and $Z^2$, and $L^1$ may be chemically bonded to each other.

Examples of the monovalent hydrocarbon group having a carbon number of from 1 to 20 include an alkyl group having a carbon number of from 1 to 20 and an aryl group having a carbon number of from 6 to 20.

Examples of the monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, include an alkyl group having a carbon number of from 1 to 20, including a substituent including the atom, an aryl group having a carbon number of from 6 to 20, including a substituent including the atom, an alkoxy group having a carbon number of from 1 to 20, and an aryloxy group having a carbon number of from 6 to 20. Examples of the substituent including the atom include a halogen atom, a hydroxy group, an alkoxy group, an aryloxy group, an amino group, an imino group, a nitrile group, an amide group, a carbamate group, a nitro group, a carboxy group, an ester group, a thioether group, a sulfo group, a phosphate group, and a silyl group.

Examples of combinations of $Z^1$, $Z^2$, and $L^1$ include the following combinations. The ligands other than $Z^1$, $Z^2$, and $L^1$ are omitted as [L].

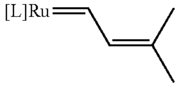
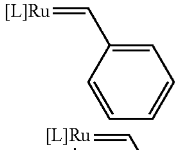
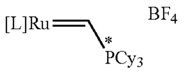
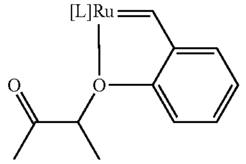
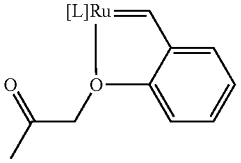
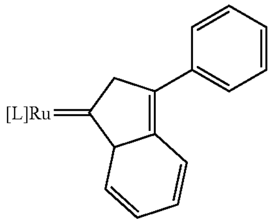
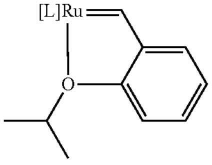
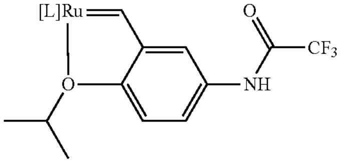
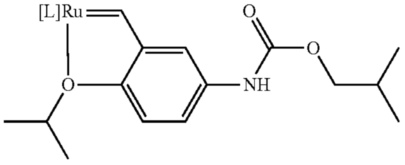
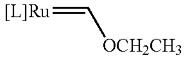
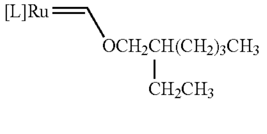
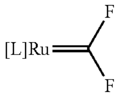
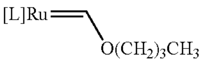
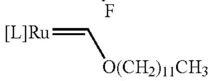

The ruthenium compound used in the method of producing a fluorine-containing olefin of the present disclosure is preferably a compound represented by the following Formula (X1) from the viewpoint of availability.

(X1)

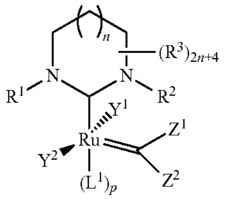

$R^1$, $R^2$, $Y^1$, $Y^2$, $L^1$, p, $Z^1$, and $Z^2$ in Formula (X1) are similar to $R^1$, $R^2$, $Y^1$, $Y^2$, $L^1$, $Z^1$, and $Z^2$ in Formula (X), respectively.

In Formula (X1), n is 1 or 2, $R^3$ represents a hydrogen atom or a substituent, and a carbon atom included in a nitrogen-containing heterocyclic ring having two nitrogen atoms may be a carbonyl carbon. Examples of the substituent represented by $R^3$ include substituents similar to the substituent included in A as described above.

Examples of the ruthenium compound represented by Formula (X) include the following compounds. "Mes" means 2,4,6-trimethylphenyl group, "o-tol" means o-tolyl group, "Dipp" means 2,6-diisopropylphenyl group, and "Cy" means cyclohexyl group.

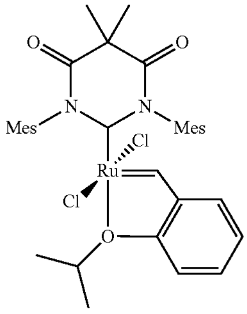

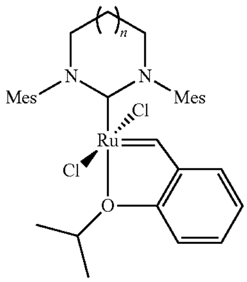

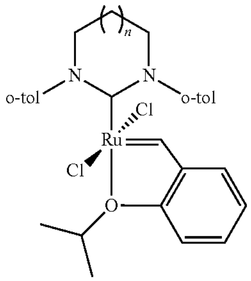

-continued

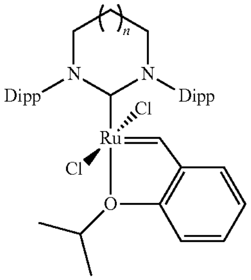

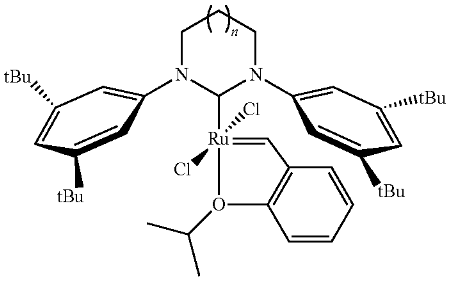

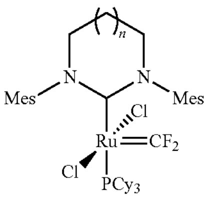

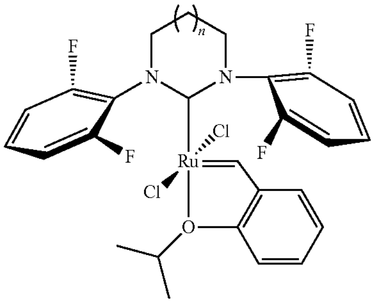

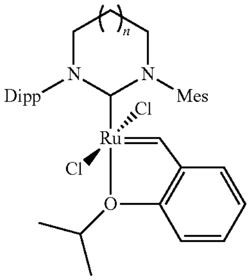

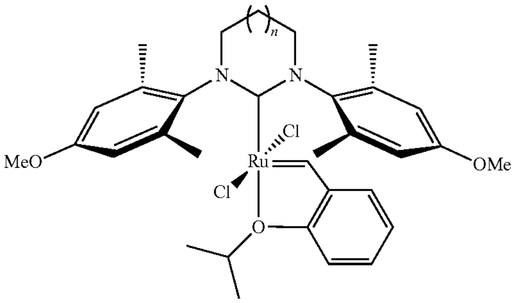

n = 1. 2

<First Olefin>

The first olefin used in the method of producing a fluorine-containing olefin of the present disclosure is an olefin represented by Formula (1).

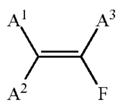

(1)

In Formula (1), each of $A^1$, $A^2$, and $A^3$ independently represents a hydrogen atom, a fluorine atom, a chlorine atom, or a fluorine-containing alkyl group having a carbon number of from 1 to 10.

Examples of the first olefin include the following compounds.

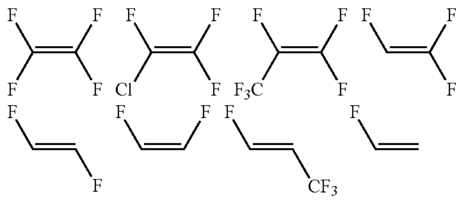

Especially, at least two of $A^1$, $A^2$, or $A^3$ in Formula (1) are preferably fluorine atoms from the viewpoint of efficiently obtaining a fluorine-containing olefin having a high fluorine content. The first olefin is preferably tetrafluoroethylene.

<Second Olefin>

The second olefin used in the method of producing a fluorine-containing olefin of the present disclosure is not particularly limited as long as the second olefin is an olefin different from the first olefin. The second olefin is preferably an olefin represented by Formula (2) from the viewpoint of improvement in yield.

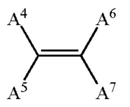

(2)

In Formula (2), at least one of $A^4$ to $A^7$ represents a functional group AA including an oxygen atom, a nitrogen atom, a sulfur atom, or a phosphorus atom at a linkage position to vinyl carbon. Each of $A^4$ to $A^7$, other than the functional group AA, independently represents a hydrogen atom, a halogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, and $A^4$ and $A^5$, $A^4$ and $A^6$, $A^5$ and $A^7$, or $A^6$ and $A^7$ may be bonded to each other to form a ring.

In a case in which one of $A^4$ or $A^5$ is a halogen atom, the other represents a hydrogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom, and in a case in which one of $A^6$ or $A^7$ is a halogen atom, the other represents a hydrogen atom, a monovalent hydrocarbon group having a carbon number of from 1 to 20, or a monovalent hydrocarbon group having a carbon number of from 1 to 20, including one or more atoms selected from the group consisting of a halogen atom, an oxygen atom, a nitrogen atom, a sulfur atom, a phosphorus atom, and a silicon atom.

Examples of the functional group AA including an oxygen atom, a nitrogen atom, a sulfur atom, or a phosphorus atom at a linkage position to vinyl carbon include an alkoxy group, an aryloxy group, an acetoxy group, an amino group, an alkylthio group, an arylthio group, a dialkylphosphino group, and a diarylphosphino group. Especially, the functional group AA is preferably a functional group including an oxygen atom, a nitrogen atom, or a sulfur atom at a linkage position to vinyl carbon from the viewpoint of improvement in yield, and more preferably an alkoxy group having a carbon number of from 1 to 20, or an aryloxy group having a carbon number of from 6 to 20.

In the second olefin, each of $A^4$ to $A^7$, other than the functional group AA, is preferably a hydrogen atom from the viewpoint of improvement in yield. The second olefin is preferably a monosubstituted olefin or a 1,2-disubstituted olefin, and more preferably a monosubstituted olefin, from the viewpoint of improvement in yield.

Examples of the second olefin include the following compounds.

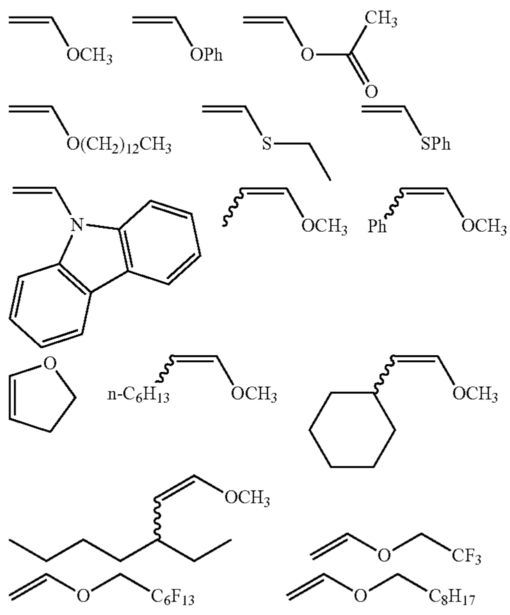

Reaction conditions in the method of producing a fluorine-containing olefin of the present disclosure is described below.

The first and second olefins used in the production method of the present disclosure are preferably degassed or dehydrated in advance from the viewpoint of improvement in yield. A degassing method is not particularly limited, and examples thereof include ultrasonic wave degassing, vacuum degassing, and freezing degassing. A dehydrating method is not particularly limited, and examples thereof include a method of contact with a dehydrating agent such as a molecular sieve.

A method of mixing the first olefin, the second olefin, and the ruthenium compound as a catalyst is not particularly limited. Examples of the mixing method include a method including dissolving the ruthenium compound in a solvent, and then sequentially adding the first olefin and the second olefin to the resultant.

The amounts of the first and second olefins used are not particularly limited, and, for example, the amount of the second olefin can be set at from 0.1 mol to 100 mol with respect to 1 mol of the first olefin.

The amount of the ruthenium compound used is preferably from 0.001% by mol to 1.0% by mol, and more preferably from 0.005% by mol to 0.5% by mol, with respect to the substance amount of the second olefin, from the viewpoint of improvement in yield. The ruthenium compound used in the method of producing a fluorine-containing olefin of the present disclosure has high catalytic activity. Therefore, the reaction can be allowed to proceed in the very small amount of the ruthenium compound used, in comparison with a case in which a ruthenium compound having a 5-membered N-heterocyclic carbene ligand is used as a catalyst.

Examples of the reaction solvent include:

- aromatic hydrocarbon solvents such as benzene, toluene, o-xylene, m-xylene, p-xylene, and mesitylene;
- aliphatic hydrocarbon solvents such as hexane and cyclohexane;
- halogen-based solvents such as dichloromethane, chloroform, 1,2-dichloroethane, chlorobenzene, and o-dichlorobenzene;
- ether-based solvents such as tetrahydrofuran, dioxane, diethyl ether, diisopropyl ether, ethylene glycol dimethyl ether, and diethylene glycol dimethyl ether; and
- ester-based solvents such as methyl acetate, ethyl acetate, isopropyl acetate, and butyl acetate.

The reaction solvent may be single, or in combination of two or more kinds thereof.

Especially, the reaction solvent is preferably an ether-based solvent or an ester-based solvent, and more preferably an ester-based solvent, from the viewpoint of improvement in yield.

The concentration of the second olefin in a reaction system is preferably low from the viewpoint of suppressing a side reaction to improve a yield, and preferably high from the viewpoint of production efficiency and a cost. From the viewpoint of both, the concentration of the second olefin in the reaction system is preferably from 0.01 mol/L to 2 mol/L, and more preferably from 0.05 mol/L to 1 mol/L. In a case in which the concentration is from 0.01 mol/L to 2 mol/L, the objective substance can be produced with high productivity and at a low cost while suppressing a by-product from being generated due to excessive proceeding of the reaction.

A reaction temperature is not particularly limited, and is preferably from 0° C. to 150° C., more preferably from 20° C. to 100° C., and still more preferably from 30° C. to 70° C. from the viewpoint of a reaction rate. Commonly, the temperature that is lower than the boiling point of the reaction solvent is set.

Reaction time is not particularly limited, is preferably from 1 hour to 15 hours, and more preferably from 2 hours to 12 hours from the viewpoint of improvement in yield. The reaction time is preferably from 2 hours to 10 hours, depending on an embodiment.

Reaction atmosphere is not particularly limited, and is preferably inert gas atmosphere. Examples of the inert gas include nitrogen and argon. Use of an olefin which is a gas under the reaction conditions, like ethylene and tetrafluoroethylene, can be performed in olefin gas atmosphere.

A pressure in the reaction system is not particularly limited, and the reaction is preferably under ordinary pressure or increased pressure from the viewpoint of improvement in yield. In the case of the increased pressure, the upper limit value of the pressure is, for example, a pressure of 4 atmospheres (atm).

In the method of producing a fluorine-containing olefin of the present disclosure, the fluorine-containing olefin which is an objective substance may be isolated by a known method. Examples of the isolation method include distillation, column chromatography, and recycling preparative HPLC, which can be used singly, or in combination of a plurality thereof, if necessary.

The obtained fluorine-containing olefin can be identified by a commonly known method. Examples of an analysis method include $^{1}H$-NMR (proton nuclear magnetic resonance), $^{19}F$-NMR (fluorine 19 nuclear magnetic resonance), $^{13}C$-NMR (carbon 13 nuclear magnetic resonance), and GC-MS (gas chromatograph mass spectrometry), which can be used singly, or in combination of a plurality thereof, if necessary.

In the method of producing a fluorine-containing olefin of the present disclosure, the reaction between the first olefin and the second olefin is excellent in functional group tolerance. In other words, even in a case in which each of the first olefin and the second olefin includes a functional group, or even in a case in which a compound having a functional group is added as an additive, the functional group is maintained without reducing reactivity, and without converting the functional group. Examples of the functional group include an alkyl group, an aromatic group, a carbonyl group, a hydroxyl group, a nitro group, an amino group, and a cyano group. The alkyl group may be a straight-chain alkyl group, a branched-chain alkyl group, or a cyclic alkyl group, and is preferably a straight-chain alkyl group. The aromatic group may be an aromatic hydrocarbon group or a heteroaromatic group, and is preferably an aromatic hydrocarbon group, and more preferably a phenyl group. The carbonyl group is preferably a carbonyl group in a ketone, an aldehyde, or an amide. The hydroxyl group is preferably an alcoholic hydroxyl group. The nitro group is preferably a nitro group bonded to an aromatic ring. The amino group is preferably a tertiary amino group. The cyano group is preferably a cyano group bonded to an aliphatic group.

EXAMPLES

The present disclosure is further specifically described below with reference to Examples. However, the present disclosure is not limited to Examples below without departing from the gist of the present disclosure.

All of a reaction conversion rate, a yield, and a selective rate in metathesis reaction were calculated using NMR. Hexafluoroparaxylene was basically used as an internal standard substance. Hexafluorobenzene and cyclohexane were used as internal standard substances in a case in which the NMR peak of hexafluoroparaxylene overlapped with the NMR peak of a raw material or an objective product. The name of a deuterated solvent was described in the case of using a deuterated solvent as a measurement solvent, while "NONE" was described in the case of measurement without using any deuterated solvent. A JNM-ECS400 (resonance frequency: 400 MHz) manufactured by JEOL Ltd. was used as an NMR apparatus. Tetramethylsilane was set at a reference value of 0 ppm in $^1$H-NMR, and $C_6F_6$ was set at a reference value of −162 ppm in $^{19}$F-NMR.

An AGILENT 7890B GC SYSTEM (manufactured by Agilent Technologies International Japan, Ltd.) was used as a gas chromatography apparatus.

The reaction conversion rate was calculated based on the following equation.

Reaction conversion rate (%)=(1−molar number of unreacted raw material/molar number of charged raw material)×100

The yield was calculated based on the following equation.

Yield (%)=(molar number of objective product/molar number of charged raw material)×100

The selective rate was calculated based on the following equation.

Selective rate (%)=(molar number of objective product/molar number of by-product)×100

Example 1

The results of metathesis reaction between tetrafluoroethylene and phenyl vinyl ether using various ruthenium catalysts are described below.

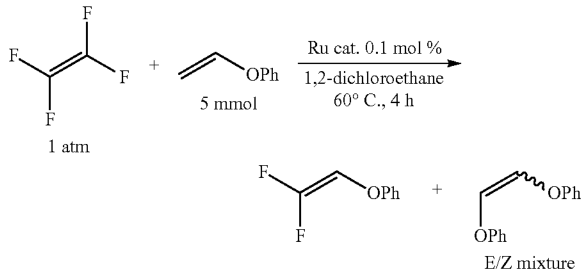

Example 1C

A solution obtained by dissolving 0.005 mmol of ruthenium catalyst (Ru-7) in 7.5 mL of 1,2-dichloroethane was prepared. The prepared solution was poured into a stainless-steel reaction container of 50 mL in capacity, including a stirring bar, a pressure gauge, an insertion pipe for gas, a raw material addition pipe, and an exhaust pipe with a back pressure valve, under nitrogen atmosphere. Then, tetrafluoroethylene was added from the insertion pipe into the reaction container at a flow rate of 6 mL/min under ordinary pressure, and substitution with the tetrafluoroethylene was performed in the reaction container. The reaction container was heated to 60° C., and a solution obtained by dissolving 5 mmol of phenyl vinyl ether in 2 mL of 1,2-dichloroethane was added for 5 minutes. After 4 hours, the reaction container was cooled to room temperature, and nitrogen gas was allowed to flow from the insertion pipe for 5 minutes at a flow rate of 25 mL/min to purge the tetrafluoroethylene. The reaction container was opened, hexafluorobenzene or hexafluoroparaxylene was added as an internal standard substance to the reaction solution, and H-NMR and $^{19}$F-NMR analysis were performed to thereby quantify raw materials and a product.

The NMR analysis results of obtained 2,2-difluorovinyl phenyl ether are described below.

$^1$H-NMR (400 MHz, chloroform-d): δ 7.31-7.36 (m, 2H), 7.08 (t, J=7.3 Hz, 1H), 7.01-7.03 (m, 2H), 6.07 (dd, J=15.1, 3.2 Hz, 1H)

$^{19}$F-NMR (376 MHz, chloroform-d): δ −97.92 (dd, J=67.9, 18.8 Hz, 1F), −116.28 (d, J=66.5 Hz, 1F)

The NMR analysis results of obtained 1,2-diphenoxyethene are described below. The mass ratio (E/Z) between an E isomer and a Z isomer was 37/63.

$^1$H-NMR (400 MHz, chloroform-d):

E body: δ 7.33 (m, 2H), 7.03-7.12 (m, 3H), 6.88 (s, 1H)

Z body: δ 7.33 (m, 2H), 7.03-7.12 (m, 3H), 6.16 (s, 1H)

Example 1A, Example 1B, Comparative Example 1

A metathesis reaction was performed by a method similar to the method in Example 1C except that a ruthenium catalyst (Ru-6) was used in Example 1A, a ruthenium catalyst (Ru-6') was used in Example 1B, and a ruthenium catalyst (Ru-5) was used in Comparative Example 1, instead of the ruthenium catalyst (Ru-7) in Example 1C.

The ruthenium catalyst (Ru-5), the ruthenium catalyst (Ru-6), the ruthenium catalyst (Ru-6'), and the ruthenium catalyst (Ru-7) are compounds having the following structures. "Mes" means 2,4,6-trimethylphenyl group (also referred to as "mesityl group").

Ru-5

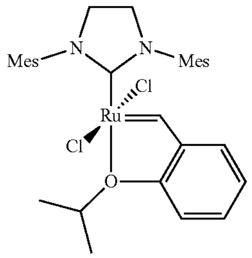

Ru-6

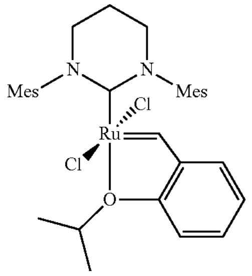

Ru-6'

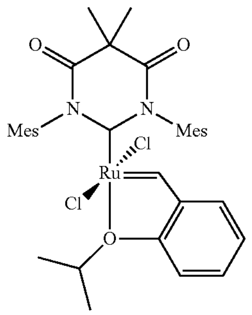

-continued

Ru-7

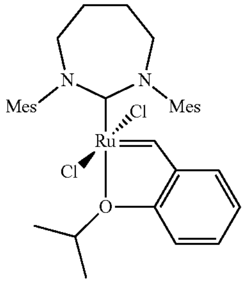

In Table 1, the reaction conversion rate (expressed as "conv." in the table) and the yield of a product in each metathesis reaction are set forth.

TABLE 1

| | Catalyst | conv. (%) | Yield (%) | |
|---|---|---|---|---|
| | | | 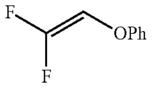 | 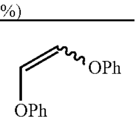 E/Z mixture |
| Comparative Example 1 | Ru-5 | 10.2 | 4.7 | trace |
| Example 1A | Ru-6 | 71.6 | 9.4 | 31.2 |
| Example 1B | Ru-6' | 19.1 | 13.5 | 2.6 |
| Example 1C | Ru-7 | 94.5 | 12.8 | 42.4 |

As set forth in Table 1, the yields of (2,2-difluorovinyl) phenyl ether which was an objective product in Examples 1A to 1C were found to be higher than that in Comparative Example 1.

Example 2

The results of performing a metathesis reaction between tetrafluoroethylene and phenyl vinyl ether under various conditions of the kinds of solvents, the amounts of solvents, the amounts of catalysts, pressures in a reaction container, reaction temperatures, and reaction times are described below.

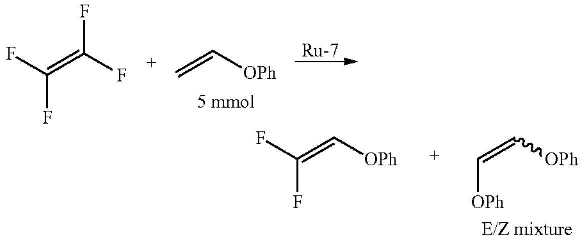

Example 2A

Example 2A is the same as Example 1C.

Examples 2B to 2F

The metathesis reaction was performed by a method similar to the method in Example 2A except that 1,2-dichloroethane used as a solvent in Example 2A was changed to a solvent set forth in Table 2.

Example 2G

The metathesis reaction was performed by a method similar to the method in Example 2F except that the reaction temperature in Example 2F was changed from 60° C. to 40° C.

Example 2G'

The metathesis reaction is performed by a method similar to the method in Example 2G except that the reaction temperature in Example 2G was changed from 40° C. to 30° C.

Example 2G"

The metathesis reaction is performed by a method similar to the method in Example 2G except that the reaction temperature in Example 2G was changed from 40° C. to 5° C.

In Example 2G' and Example 2G", a decrease in the reaction temperature facilitates stop of the reaction at a low conversion rate, as a result of which improvement in the selective rate is expected.

Example 2H

The metathesis reaction was performed by a method similar to the method in Example 2F except that the back pressure valve was adjusted so that the pressure in the reaction container was a pressure of 2 atmospheres in Example 2F.

Example 2H'

The metathesis reaction is performed by a method similar to the method in Example 2H except that the back pressure valve is adjusted so that the pressure in the reaction container is a pressure of 4 atmospheres in Example 2H.

In Example 2H', an increase in the pressure is expected to result in improvement in the reaction conversion rate, the yield, and the selective rate.

Example 2I

A solution obtained by dissolving 0.005 mmol of ruthenium catalyst (Ru-7) in 38 mL of ethyl acetate was prepared. The prepared solution was poured into a stainless-steel reaction container of 50 mL in capacity, including a stirring bar, a pressure gauge, an insertion pipe for gas, a raw material addition pipe, and an exhaust pipe with a back pressure valve, under nitrogen atmosphere. Then, tetrafluoroethylene was added from the insertion pipe into the reaction container at a flow rate of 6 mL/min, and substitution with the tetrafluoroethylene was performed in the reaction container. The back pressure valve was adjusted so that the pressure in the reaction container was a pressure of 2 atmospheres. The reaction container was heated to 60° C., and a solution obtained by dissolving 5 mmol of phenyl vinyl ether in 2 mL of ethyl acetate was added for 5 minutes. After 8 hours, the reaction container was cooled to room temperature, and nitrogen gas was allowed to flow from the insertion pipe for 5 minutes at a flow rate of 25 mL/min to purge the tetrafluoroethylene. The reaction container was opened, hexafluorobenzene or hexafluoroparaxylene was added as an internal standard substance to the reaction solution, and $^{1}$H-NMR and $^{19}$F-NMR analysis were performed to thereby quantify raw materials and a product.

Example 2J

The metathesis reaction was performed by a method similar to the method in Example 2I except that the amount of the ruthenium-catalyst (Ru-7) was changed to 0.0005 mmol, and the reaction time was changed to 12 hours in Example 2I.

Example 2J'

The metathesis reaction is performed by a method similar to the method in Example 2J except that the amount of the ruthenium catalyst (Ru-7) is changed to 0.05 mmol in Example 2J.

Example 2J"

The metathesis reaction is performed by a method similar to the method in Example 2J except that the amount of the ruthenium catalyst (Ru-7) is changed to 0.00025 mmol in Example 2J.

In Example 2J' and Example 2J", a decrease in the amount of the ruthenium catalyst facilitates stop of the reaction at a low conversion rate, as a result of which improvement in the selective rate is expected.

In Table 2, the reaction conversion rate (expressed as “conv.” in the table), and the yield and selective rate of a product in each metathesis reaction are set forth. In Table 2, DCE means 1,2-dichloroethane, THF means tetrahydrofuran, $iPr_2O$ means diisopropyl ether, CPME means cyclopentyl methyl ether, and EtOAc means ethyl acetate. The selective rate was calculated based on the molar number of 1,2-diphenoxyethene which was a side-product and the molar number of 2,2-difluorovinyl phenyl ether which was an objective product.

TABLE 2

| | Solvent | | | | | | | Yield (%) | | |
|---|---|---|---|---|---|---|---|---|---|---|
| | Kind | Amount (mL) | Amount of catalyst (% by mol) | Pressure (atm) | Time (h) | Temperature (° C.) | conv. (%) | 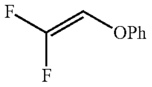 [SMILES: FC(F)=COc1ccccc1] | 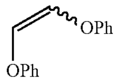 E/Z mixture | Selective rate |
| Example 2A | DCE | 9.5 | 0.1 | 1 | 4 | 60 | 94.5 | 12.8 | 42.4 | 0.30 |
| Example 2B | THF | 9.5 | 0.1 | 1 | 4 | 60 | 75.1 | 19.3 | 21.9 | 0.88 |
| Example 2C | Toluene | 9.5 | 0.1 | 1 | 4 | 60 | 98.6 | 24.9 | 40.8 | 0.61 |
| Example 2D | $iPr_2O$ | 9.5 | 0.1 | 1 | 4 | 60 | 58.8 | 13.2 | 19.4 | 0.68 |
| Example 2E | CPME | 9.5 | 0.1 | 1 | 4 | 60 | 94.6 | 32.6 | 28.2 | 1.16 |
| Example 2F | EtOAc | 9.5 | 0.1 | 1 | 4 | 60 | 98.8 | 34.4 | 37.0 | 0.93 |
| Example 2G | EtOAc | 9.5 | 0.1 | 1 | 4 | 40 | 86.2 | 47.6 | 25.5 | 1.87 |
| Example 2H | EtOAc | 9.5 | 0.1 | 2 | 4 | 60 | 97.7 | 46.0 | 20.3 | 2.27 |
| Example 2I | EtOAc | 40.0 | 0.1 | 2 | 8 | 60 | 91.2 | 73.4 | 7.8 | 9.41 |
| Example 2J | EtOAc | 40.0 | 0.01 | 2 | 12 | 60 | 61 | 40.7 | 2.3 | 17.70 |

As set forth in Table 2, the yields of 2,2-difluorovinyl phenyl ether which was the objective product in Examples 2B to 2J were found to be as high as that in Example 2A (Example 1C). The yield and selective rate of 2,2-difluorovinyl phenyl ether which was the objective product were found to be high particularly in the case of using the ether-based solvent or the ester-based solvent. Comparison between Example 2G and Example 2H revealed that the higher pressure of tetrafluoroethylene resulted in the higher yield and selective rate of 2,2-difluorovinyl phenyl ether which was the objective product. Comparison between Example 2H and Example 2I revealed that the lower concentration of phenyl vinyl ether which was a second olefin resulted in the higher yield and selective rate of 2,2-difluorovinyl phenyl ether which was the objective product.

Example 3

The results of performing metathesis reactions between tetrafluoroethylene and monosubstituted olefins using the various monosubstituted olefins are described below.

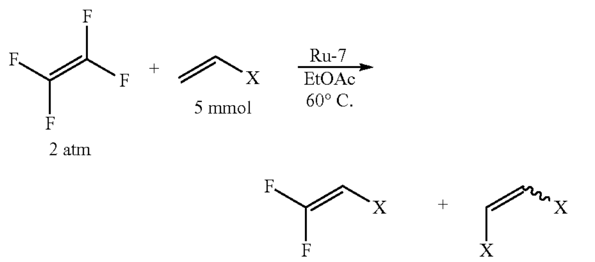

31

32 E/Z mixture

Example 3A

Example 3A is the same as Example 2I.

Examples 3B to 3E

The metathesis reaction was performed by a method similar to the method in Example 3A except that the phenyl vinyl ether used in Example 3A was changed to monosubstituted olefins set forth in Table 3, and the amount of a solvent, the amount of a catalyst, and reaction time were changed to conditions in Table 3. In Example 3E, 2.5 mmol of the monosubstituted olefin was used.

In Table 3, the reaction conversion rate (expressed as "conv." in the table), and the yield and selective rate of a product (compound 31) in each metathesis reaction are set forth. In Table 3, Ph means phenyl group. The selective rate was calculated based on the molar number of the compound 31 which was an objective product and the molar number of a compound 32 which was a side-product.

The NMR analysis results of 2,2-difluorovinyl dodecyl ether obtained in Example 3B are described below.

$^{1}$H-NMR (400 MHz, chloroform-d): δ 5.62 (dd, J=16.7, 2.5 Hz, 1H), 3.68 (t, J=6.6 Hz, 2H), 1.59-1.66 (m, 2H), 1.26-1.41 (m, 19H), 0.88 (t, J=6.9 Hz, 3H)

$^{19}$F-NMR (376 MHz, chloroform-d): δ −101.28 (dd, J=80.9, 17.3 Hz, 1F), −121.53 (d, J=80.9 Hz, 1F).

The NMR analysis results of 2,2-difluorovinyl phenyl sulfide obtained in Example 3C are described below.

$^{1}$H-NMR (400 MHz, chloroform-d): δ 7.29-7.31 (m, 4H), 7.19-7.24 (m, 1H), 5.15 (d, J=21.0 Hz, 1H)

$^{19}$F-NMR (376 MHz, chloroform-d): δ −76.55 (d, J=19.0 Hz, 1F), −79.48 (dd, J=20.8, 19.0 Hz, 1F)

The NMR analysis results of N-(2,2-difluorovinyl)carbazole obtained in Example 3D are described below.

$^{19}$F-NMR (376 MHz, NONE): δ −103.37 (dd, J=83.8, 14.4 Hz, 1F), −124.10 (d, J=86.7 Hz, 1F)

The NMR analysis results of 2,2-difluorovinyl tridecafluoroheptyl ether obtained in Example 3E are described below.

$^{19}$F-NMR (376 MHz, chloroform-d): δ −80.64 (s, 3F), −96.70 (dd, J=72.2 Hz, 14.4 Hz, 1F), −117.59 (d, J=75.1 Hz, 1F), −120.02 (s, 2F), −122.11 (s, 2F), −122.74 (s, 2F), −123.32 (s, 2F), −126.04 (s, 2F)

TABLE 3

| | X | Time (h) | Solvent (mL) | Amount of catalyst (% by mol) | conv. (%) | Yield (%) 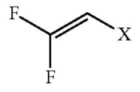 | Selective rate |
|---|---|---|---|---|---|---|---|
| Example 3A | OPh | 8 | 40 | 0.1 | 91.2 | 73.4 | 9.41 |
| Example 3B | $OC_{12}H_{25}$ | 5 | 40 | 0.1 | 100 | 92.8 | 10.8 |
| Example 3C | SPh | 5 | 9.5 | 0.1 | 61.4 | 33.2 | 3.05 |
| Example 3D | 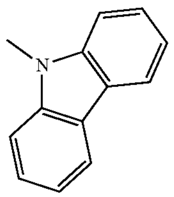 | 2 | 9.5 | 0.1 | 1.5 | 0.8 | — |
| Example 3E | $OCH_2C_6F_{13}$ | 8 | 9.5 | 0.2 | 98 | 59 | 3.7 |

As set forth in Table 3, the metathesis reaction was found to proceed in the case of using any monosubstituted olefin described in Examples 3A to 3E.

Example 4

The results of performing metathesis reactions between tetrafluoroethylene and 1,2-disubstituted olefins using the various 1,2-disubstituted olefins are described below.

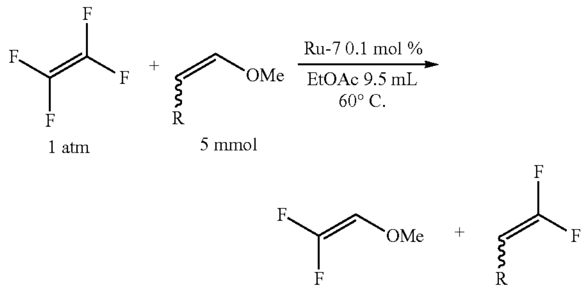

1 atm 5 mmol

41

42

Examples 4A to 4B

The metathesis reaction was performed by a method similar to the method in Example 2F except that the phenyl vinyl ether used in Example 2F was changed to 1,2-disubstituted olefins set forth in Table 4, and the reaction time was changed to times set forth in Table 4.

In Table 4, the reaction conversion rate (expressed as “conv.” in the table), and the yield of a product (compound 42) in each metathesis reaction are set forth. In Table 4, Ph means phenyl group, and n-Hep means n-heptyl group.

TABLE 4

| | R | Time (h) | conv. (%) | Yield % 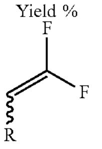 |
|---|---|---|---|---|
| Example 4A | Ph (E/Z = 47/53) | 8 | 24.4 | 23.6 |
| Example 4B | n-Hep (E/Z = 46/54) | 9 | 92.2 | 85.2 |

As set forth in Table 4, the metathesis reaction was found to proceed in the case of using any 1,2-disubstituted olefin described in Examples 4A and 4B.

Example 5

The results of a metathesis reaction between tetrafluoroethylene and a cyclic olefin are described below.

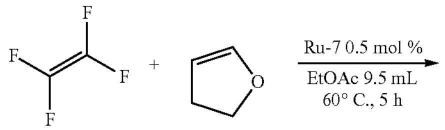

1 atm 5 mmol

-continued

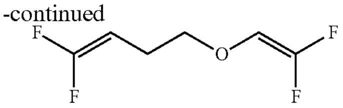

51

Example 5A

The metathesis reaction was performed by a method similar to the method in Example 2F except that the phenyl vinyl ether used in Example 2F was changed to 2,3-dihydrofuran, the amount of the ruthenium catalyst (Ru-7) used was changed to 0.5% by mol, and the reaction time was changed to 5 hours.

$^{19}$F-NMR analysis provided confirmation that a compound 51 was obtained.

$^{19}$F-NMR (376 MHz, NONE): δ −87.70 (d, J=49.1 Hz, 1F), −90.44 (dd, J=46.2, 23.1 Hz, 1F), −101.58 (dd, J=86.7, 17.3 Hz, 1F), −121.93 (d, J=86.7 Hz, 1F)

Example 6

A functional group tolerance test was conducted for the metathesis reaction between tetrafluoroethylene and phenyl vinyl ether.

Tetrafluoroethylene at 1 atm was filled into a screw cap NMR tube, followed by adding a ruthenium catalyst (Ru-7). After addition of a solution obtained by dissolving 220 μmol of phenyl vinyl ether and 1,4-bis(trifluoromethyl)benzene which was an internal standard substance in 0.6 mL of toluene, each additive set forth in Table 5 was added so that the additive was 1 equivalent with respect to the phenyl vinyl ether, and the NMR tube was heated at 60° C. for 2 hours. After 2 hours, the NMR tube was cooled to room temperature. In Example 5A, raw materials and a product were quantified by performing $^{1}$H-NMR and $^{19}$F-NMR analysis. In Examples 5B to 5H, raw materials and products were quantified by using gas chromatography.

In Table 5, the reaction conversion rate (expressed as “conv.” in the table), the yield of a product, and the residual amount of additive in each metathesis reaction are set forth. In Table 5, MeCN means acetonitrile, and EtOH means ethanol. The residual amount of additive was calculated based on the following equation.

Residual amount (%) of additive=(amount of additive after reaction/amount of charged additive)×100

In Examples 5B to 5H, the amount (molar number) of additive after the reaction was calculated using a gas chromatography apparatus.

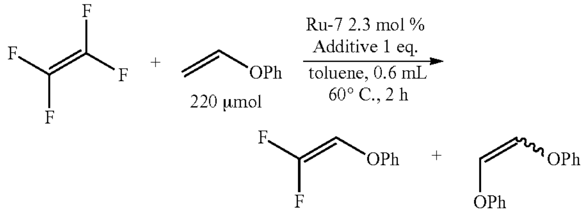

E/Z mixture

TABLE 5

| | | | Yield (%) | | |
|---|---|---|---|---|---|
| | Additive | conv. (%) | 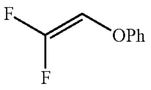 | 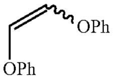 E/Z mixture | Residual amount of additive (%) |
| Example 5A | — | 45 | 5.3 | 21 | — |
| Example 5B | 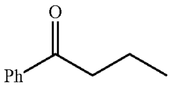 | 46 | 4.9 | 22 | 100 |
| Example 5C | 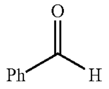 | 41 | 8.5 | 18 | 93 |
| Example 5D | EtOH | 39 | 6.6 | 17 | 81 |
| Example 5E | 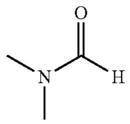 | 35 | 8.1 | 14 | 93 |
| Example 5F | $NEt_3$ | 17 | 9.3 | 3.1 | 88 |
| Example 5G | MeCN | 7.7 | 5.3 | 1.0 | 90 |
| Example 5H | 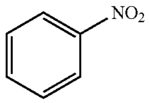 | 37 | 8.2 | 16.0 | 100 |

As described in Examples 5B to 5H, the metathesis reaction was found to proceed even in a case in which a compound having a functional group was added as an additive.

The entireties of the disclosures by Japanese Patent Application No. 2020-034736 filed on Mar. 2, 2020, and Japanese Patent Application No. 2020-132483 filed on Aug. 4, 2020 are incorporated herein by reference. All documents, patent applications, and technical standards described in this specification are herein incorporated by reference to the same extent as if each individual document, patent application, or technical standard was specifically and individually indicated to be incorporated by reference.

What is claimed is:

1. A production method of producing a fluorine-containing olefin comprising:

allowing a first olefin represented by the following Formula (1) and a second olefin different from Formula (1) of the first olefin to react with each other in the presence of a ruthenium compound represented by the following Formula (X):

(X)

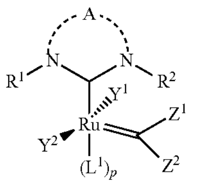

wherein, in Formula (X),

A represents an atom group necessary for forming a 6- or 7-membered nitrogen-containing heterocyclic ring comprising two nitrogen atoms, an aromatic or aliphatic ring may be condensed to the nitrogen-containing heterocyclic ring, and A and the aromatic or aliphatic ring condensed to the nitrogen-containing heterocyclic ring may comprise a substituent, each of $R^1$ and $R^2$ independently represents an alkyl group, an aryl group, or an aralkyl group, each of $Y^1$ and $Y^2$ independently represents an anionic ligand, L' represents a neutral electron-donating ligand, p represents 0 or 1, and each of $Z^1$ and $Z^2$ independently represents a hydrogen atom, a halogen atom, a monovalent hydrocarbon group having a carbon number of from 1 to 20, or a monovalent hydrocarbon group having a carbon number of from 1 to 20 and comprising one or more atoms selected from the group consisting of a halogen atom, an oxygen atom, a nitrogen atom, a sulfur atom, a phosphorus atom, and a silicon atom, $Z^1$ and $Z^2$ may be bonded to each other to form a ring, and either or both of $Z^1$ and $Z^2$, and $L^1$ may be chemically bonded to each other,

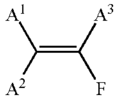

(1)

wherein, in Formula (1), each of $A^1$, $A^2$, and $A^3$ independently represents a hydrogen atom, a fluorine atom, a chlorine atom, or a fluorine-containing alkyl group having a carbon number of from 1 to 10.

2. The production method according to claim 1, wherein the second olefin is represented by the following Formula (2):

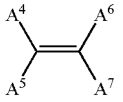

(2)

wherein, in Formula (2), at least one of $A^4$ to $A^7$ represents a functional group AA comprising an oxygen atom, a nitrogen atom, a sulfur atom, or a phosphorus atom at a linkage position to vinyl carbon, each of $A^4$ to $A^7$, other than the functional group AA, independently represents a hydrogen atom, a halogen atom, a monovalent hydrocarbon group having a carbon number of from 1 to 20, or a monovalent hydrocarbon group having a carbon number of from 1 to 20 and comprising one or more atoms selected from the group consisting of a halogen atom, an oxygen atom, a nitrogen atom, a sulfur atom, a phosphorus atom, and a silicon atom, and $A^4$ and $A^5$, $A^4$ and $A^6$, $A^5$ and $A^7$, or $A^6$ and $A^7$ may be bonded to each other to form a ring, and in a case in which one of $A^4$ or $A^5$ is a halogen atom, another one of $A^4$ or $A^5$ represents a hydrogen atom, a monovalent hydrocarbon group having a carbon number of from 1 to 20, or a monovalent hydrocarbon group having a carbon number of from 1 to 20 and comprising one or more atoms selected from the group consisting of a halogen atom, an oxygen atom, a nitrogen atom, a sulfur atom, a phosphorus atom, and a silicon atom, and in a case in which one of $A^6$ or $A^7$ is a halogen atom, another one of $A^6$ or $A^7$ represents a hydrogen atom, a monovalent hydrocarbon group having a carbon number of from 1 to 20, or a monovalent hydrocarbon group having a carbon number of from 1 to 20 and comprising one or more atoms selected from the group consisting of a halogen atom, an oxygen atom, a nitrogen atom, a sulfur atom, a phosphorus atom, and a silicon atom.

3. The production method according to claim 2, wherein, in Formula (2), the functional group AA is an alkoxy group having a carbon number of from 1 to 20 or an aryloxy group having a carbon number of from 6 to 20.

4. The production method according to claim 1, wherein, in Formula (1), at least two of $A^1$, $A^2$, or $A^3$ are fluorine atoms.

5. The production method according to claim 1, wherein the second olefin is a monosubstituted olefin or a 1,2-disubstituted olefin.

6. The production method according to claim 1, wherein an amount of the ruthenium compound used is from 0.001% by mol to 1.0% by mol with respect to a substance amount of the second olefin.

7. The production method according to claim 1, wherein, in Formula (X), each of $R^1$ and $R^2$ is independently 2,4,6-trimethylphenyl group, 2,6-diisopropylphenyl group, o-tolyl group, 3,5-di-tert-butylphenyl group, 2,6-dimethyl-4-methoxyphenyl group, or 2,6-difluorophenyl group.

8. The production method according to claim 1, wherein A is an atom group that forms a 6-membered nitrogen-containing heterocyclic ring.

9. The production method according to claim 1, wherein A is an atom group that forms a 7-membered nitrogen-containing heterocyclic ring.

10. The production method according to claim 1, wherein the first olefin and the second olefin react with each other under an olefin back pressure of 1 to 2 atm.

11. The production method according to claim 1, wherein the first olefin and the second olefin react with each other in the presence of the ruthenium compound to form the fluorine-containing olefin with a reaction conversion rate of 19.1 to 71.6%.

12. The production method according to claim 1, wherein the first olefin and the second olefin react with each other in the presence of the ruthenium compound to form the fluorine-containing olefin with a reaction conversion rate of 58.8 to 98.8%.

13. The production method according to claim 1, wherein the first olefin and the second olefin react with each other in the presence of the ruthenium compound to form the fluorine-containing olefin with a selective rate of 3.05 to 10.8.

14. The production method according to claim 1, wherein the first olefin and the second olefin react with each other in the presence of the ruthenium compound to form the fluorine-containing olefin with a selective rate of 0.3 to 17.7.

15. The production method according to claim 1, wherein the functional group AA is selected from the group consisting of an alkoxy group, an aryloxy group, an acetoxy group, an amino group, an alkythio group, an arylthio group, a dialkyphosphino group and a diarylphosphino group.

* * * * *